United States Patent [19]

Ferrante et al.

[11] Patent Number: 5,709,689
[45] Date of Patent: Jan. 20, 1998

[54] DISTAL FEMUR MULTIPLE RESECTION GUIDE

[75] Inventors: Joseph M. Ferrante, Bartlett; Rodney L. Houfburg, Cordova, both of Tenn.

[73] Assignee: Wright Medical Technology, Inc., Arlington, Tenn.

[21] Appl. No.: 533,339

[22] Filed: Sep. 25, 1995

[51] Int. Cl.$^6$ ............................ A61B 17/00; A61B 17/58; A61F 5/00
[52] U.S. Cl. ..................... 606/86; 606/80; 606/87; 606/88
[58] Field of Search ................... 606/88, 87, 86, 606/96, 102

[56] References Cited

U.S. PATENT DOCUMENTS

| | | |
|---|---|---|
| 4,722,330 | 2/1988 | Russell et al. ............... 606/88 X |
| 4,738,253 | 4/1988 | Buechel et al. ............... 606/96 X |
| 4,759,350 | 7/1988 | Dunn et al. . |
| 4,773,407 | 9/1988 | Petersen ............... 606/88 X |
| 4,892,093 | 1/1990 | Zarnowski et al. ............... 606/88 |
| 4,907,578 | 3/1990 | Petersen ............... 606/88 |
| 4,935,023 | 6/1990 | Whiteside et al. ............... 606/88 |
| 5,129,909 | 7/1992 | Sutherland . |
| 5,364,401 | 11/1994 | Ferrante et al. ............... 606/88 |

FOREIGN PATENT DOCUMENTS

| | | | |
|---|---|---|---|
| 340176 | 11/1989 | European Pat. Off. ............... 606/88 |
| 466659 | 1/1992 | European Pat. Off. ............... 606/88 |
| 538153 | 4/1993 | European Pat. Off. ............... 606/88 |
| 555003 | 8/1993 | European Pat. Off. ............... 606/88 |

OTHER PUBLICATIONS

*Total Condylar & Posterior Stabilized Surgical Technique*, ORTHOLOC® ADVANTIM™, Wright Medical Technology, Inc., 1993 Author unknown.

Primary Examiner—Michael Buiz
Assistant Examiner—Julian W. Woo
Attorney, Agent, or Firm—Walker, McKenzie & Walker, P.C.

[57] ABSTRACT

A distal femur multiple resection guide for attachment to a distal femur having a resected anterior surface and a resected distal surface, and for guiding a cutting tool. The multiple resection guide includes a block member having a distal femoral resection contact surface for placement against the resected distal surface of the distal femur; an arm member having an anterior resection contact surface for placement against the resected anterior surface of the distal femur; an anterior bevel cut guide on the block member for guiding the cutting tool to make an anterior bevel cut on the distal femur; a posterior bevel cut guide on the block member for guiding the cutting tool to make a posterior bevel cut on the distal femur; a posterior condyle cut guide on the block member for guiding the cutting tool to make a posterior condyle cut on the distal femur; and patellar track cut guide on the arm member for guiding the cutting tool to make a patellar track cut on the distal femur.

13 Claims, 3 Drawing Sheets

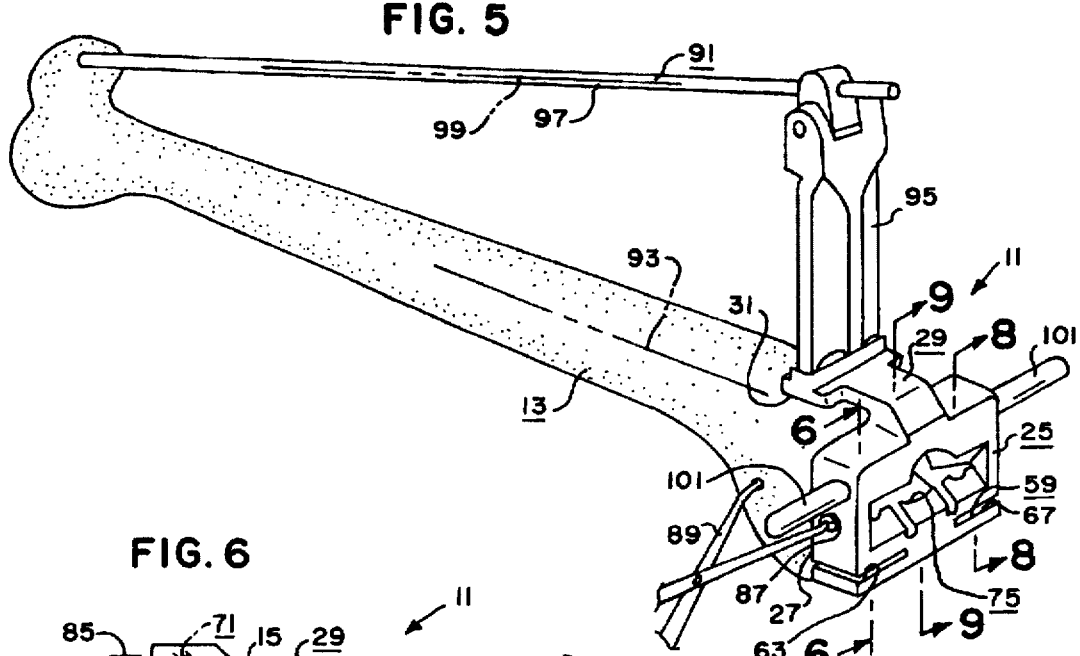
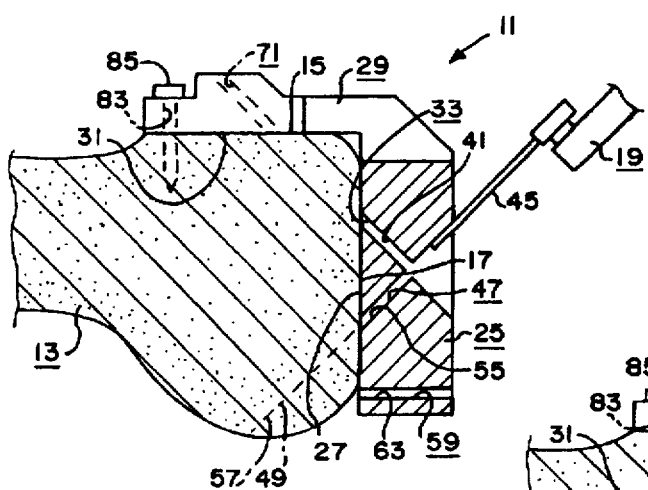
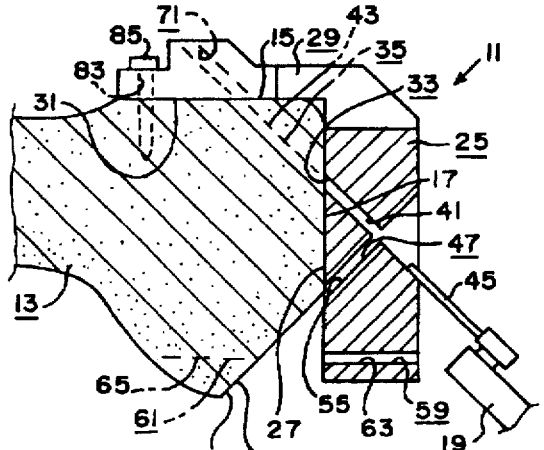
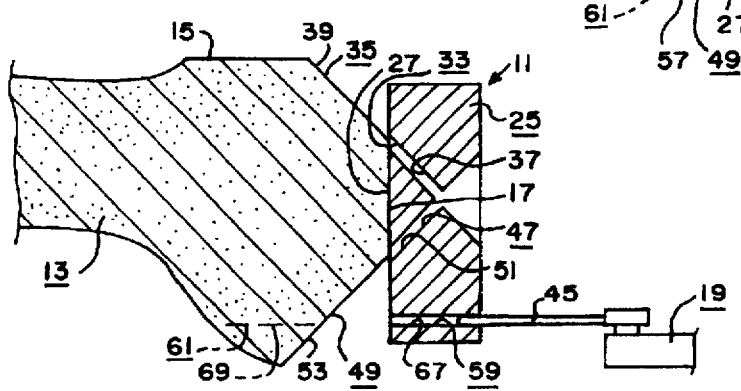

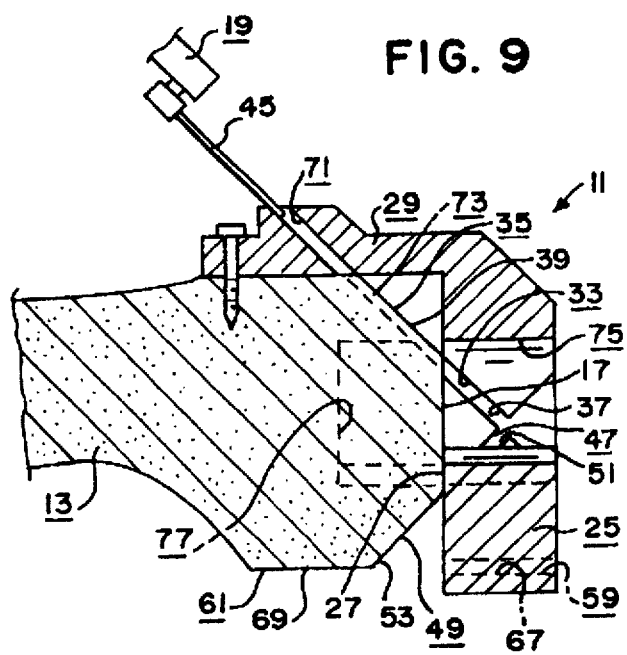
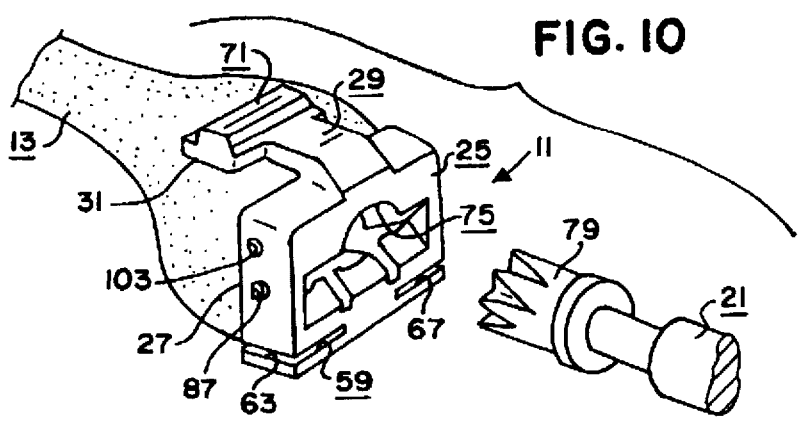
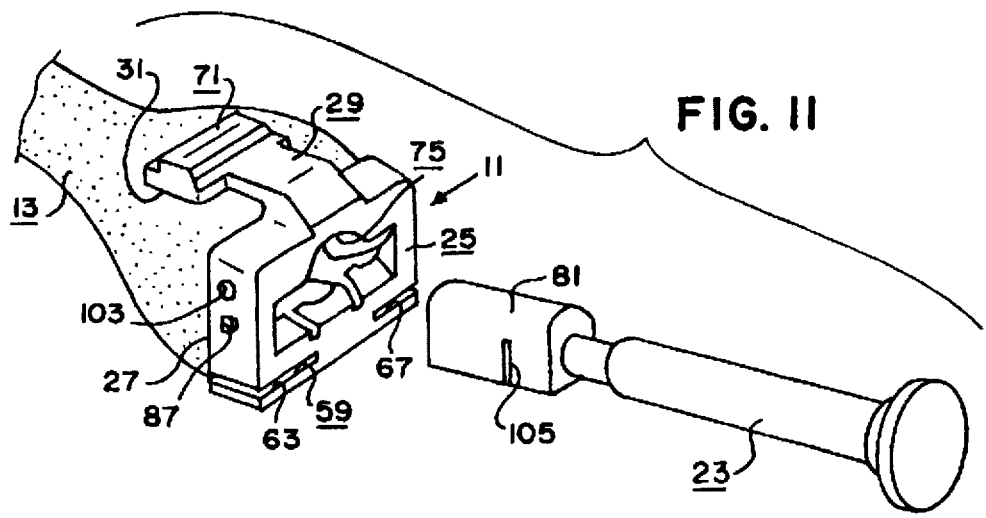

DISTAL FEMUR MULTIPLE RESECTION GUIDE

BACKGROUND OF THE INVENTION

1. Field of the Invention

The present invention relates, in general, to a guide for regulating or directing multiple resections of a distal femur to prepare that distal femur for a prosthetic implant.

2. Information Disclosure Statement

In order to implant a distal femoral prosthesis on a distal femur, certain substantially "standard" resections or cuts are made to the distal femur. As will be apparent to those skilled in the art, these substantially "standard" resections or cuts include: (1) a distal femoral cut to remove a portion of the distal end of the femur substantially equal to the thickness to be replaced by the distal condyle of the prosthesis unless special ligament problems dictate otherwise, etc.; (2) an anterior flange or condylar cut to remove a portion of the anterior condyles; (3) a medial anterior bevel cut to remove an angular portion of the media condyle between the distal femoral cut and the anterior condylar cut; (4) a lateral anterior bevel cut to remove an angular portion of the lateral condyle between the distal femoral cut and the anterior condylar cut; (5) a medial posterior condylar cut to remove a portion of the medial posterior condyles; (6) a lateral posterior condylar cut to remove a portion of the lateral posterior condyles; (7) a media posterior bevel cut to remove an angular portion of the medial condyle between the distal femoral cut and the medial posterior condylar cut; (8) a lateral posterior bevel cut to remove an angular portion of the lateral condyle between the distal femoral cut and the lateral posterior condylar cut; (9) a patellar track groove cut to create or enhance the shallow groove in the femoral patellar groove to accommodate the recessed patellar track of the femoral prosthesis; and, if desired or necessary, (10) a posterior stabilized cut to create a cavity for receiving the housing of a posterior stabilized femoral prosthesis.

Surgical techniques and instrumentation for preparing a distal femur to receive a distal implant prosthesis are disclosed in the document, *Total Condylar & Posterior Stabilized Surgical Technique, ORTHOLOC® ADVANTIM™*, Wright Medical Technology, Inc. (1993). As disclosed therein, nine or ten resections may be made to a distal femur to prepare that distal femur to receive a distal femur implant prosthesis. In general, after preoperative planning to estimate the size of prosthesis to be implanted, etc., and after the distal femur is exposed and sized, etc., a distal femoral cut guide is positioned on the distal femur a the distal femoral cut is made using an oscillating saw as disclosed at pages 7–9 of the *Total Condylar & Posterior Stabilized Surgical Technique, ORTHOLOC® ADVANTIM™* publication. The distal femoral cut guide is then removed and an anterior/posterior (A/P) bevel cut guide is seated flush against the distal femoral cut using bone claims and/or nails, Steinmann pins, etc., and an anterior condyle or flange cut is made using a wide saw blade and the A/P bevel cut guide as disclosed at pages 11–12 of the *Total Condylar & Posterior Stabilized Surgical Technique, ORTHOLOC® ADVANTIM™* publication. A medial anterior bevel cut is made using the wide saw blade and using a wide saw blade and the A/P bevel cut guide as disclosed at pages 11–12 of the *Total Condylar & Posterior Stabilized Surgical Technique, ORTHOLOC® ADVANTIM™* publication. A lateral anterior bevel cut is made using the wide saw blade and using a wide saw blade and the A/P bevel cut guide as disclosed at pages 11–12 of the *Total Condylar & Posterior Stabilized Surgical Technique, ORTHOLOC® ADVANTIM™* publication. A medial posterior bevel cut is made using a narrow saw blade and the A/P bevel cut guide as disclosed at pages 11–12 of the *Total Condylar & Posterior Stabilized Surgical Technique, ORTHOLOC® ADVANTIM™* publication. A lateral posterior bevel cut is made using the narrow saw blade and the A/P bevel cut guide as disclosed at pages 11–12 of the *Total Condylar & Posterior Stabilized Surgical Technique, ORTHOLOC® ADVANTIM™* publication. A medial posterior condyle cut is made using the narrow saw blade and the A/P bevel cut guide as disclosed at pages 11–12 of the *Total Condylar & Posterior Stabilized Surgical Technique, ORTHOLOC® ADVANTIM™* publication. A lateral posterior condyle cut is made using the narrow saw blade and the A/P bevel cut guide as disclosed at pages 11–12 of the *Total Condylar & Posterior Stabilized Surgical Technique, ORTHOLOC® ADVANTIM™* publication. The A/P bevel cut guide is then removed and a patellar track positioner is fixed to the distal femur to guide a cutting tool, such as a powered patellar track burr, to cut or resect a patellar track groove in the distal femur to accommodate the recessed patellar track of the final femoral implant prosthesis as disclosed at page 18 of the *Total Condylar & Posterior Stabilized Surgical Technique, ORTHOLOC® ADVANTIM™* publication. If it is desired to implant a posterior stabilized femoral prosthesis, a posterior stabilized endmill guide is secured to the patellar track positioner, a posterior stabilized endmill cutter is then used with the posterior stabilized endmill guide to cut or resect a posterior stabilized cut in the distal femur to accommodate the posterior stabilized housing as disclosed at pages 42–43 of the *Total Condylar & Posterior Stabilized Surgical Technique, ORTHOLOC® ADVANTIM™* publication. A housing punch may be used with the posterior stabilized endmill guide to remove any remaining bone posterior to the endmill cut. Alternatively, a rongeur or saw may also be used after the posterior stabilized endmill guide is removed.

Dunn et al., U.S. Pat. No. 4,759,350, issued Jul. 26, 1988, discloses a system of instruments for preparing a distal femur to receive a distal implant prosthesis.

Sutherland, U.S. Pat. No. 5,129,909, issued Jul. 14, 1992, discloses an apparatus and method for making precise bone cuts in a distal femur.

None of these patents or references disclose or suggest the present invention. More specifically, none of these patents or references disclose or suggest a distal femur multiple resection guide including a block member having a distal femoral resection contact surface for placement against a resected distal surface of a distal femur; an arm member having an anterior resection contact surface for placement against a resected anterior surface of the distal femur; anterior bevel cut guide means on the block member for guiding the cutting tool to make an anterior bevel cut on the distal femur; posterior bevel cut guide means on the block member for guiding the cutting tool to make a posterior bevel cut on the distal femur; posterior condyle cut guide means on the block member for guiding the cutting tool to make a posterior condyle cut on the distal femur; and patellar track cut guide means on the arm member for guiding the cutting tool to make a patellar track cut on the distal femur.

SUMMARY OF THE INVENTION

The present invention provides a guide for regulating or directing multiple resections of a distal femur to prepare that distal femur for a prosthetic implant. A basic concept of the present invention is to provide a distal femur multiple resection guide that reduces the surgical steps needed in order to prepare a distal femur to receive an implant prosthesis, and that allows the necessary resections to be more accurately made than with present resection guides.

The distal femur multiple resection guide of the present invention comprises, in general, a block member having a distal femoral resection contact surface for placement against a resected distal surface of a distal femur; an arm member having an anterior resection contact surface for placement against a resected anterior surface of the distal femur; anterior bevel cut guide means on the block member for guiding the cutting tool to make an anterior bevel cut on the distal femur; posterior bevel cut guide means on the block member for guiding the cutting tool to make a posterior bevel cut on the distal femur; posterior condyle cut guide means on the block member for guiding the cutting tool to make a posterior condyle cut on the distal femur; and patellar track cut guide means on the arm member for guiding the cutting tool to make a patellar track cut on the distal femur.

One object of the present invention is to provide a distal femur multiple resection guide for use in preparing the box cuts for the distal femur to receive an implant prosthesis.

Another object of the present invention is to provide a distal femur multiple resection guide that incorporates an end mill guide means in order to allow for preparation of a posterior stabilized housing after resection of the anterior and distal femoral cuts.

Another object of the present invention is to provide a distal femur multiple resection guide with an anterior flange or arm having either an opened or closed cutting slot placed at the appropriate angle to remove bone by use of a cutting means such that a trochlear groove is prepared.

Another object of the present invention is to provide a distal femur multiple resection guide that combines features of three separate instrumentations into one instrument to reduce surgical steps and to more accurately prepare the bone for the prosthesis.

Another object of the present invention is to provide a distal femur multiple resection guide having a medial/lateral width and an anterior/posterior depth which replicates the implant size so that the implant features can be positioned on the bone.

BRIEF DESCRIPTION OF THE DRAWINGS

FIG. 5 is a diagrammatic perspective view of the distal femur multiple resection guide of the present invention shown being properly aligned on and attached to a femur with the femur shown separate from the patient's body for clarity.

FIG. 6 is a sectional view of a portion of the distal femur multiple resection guide of the present invention shown attached to a distal femur and showing a reciprocating saw being guided to make a posterior bevel cut.

FIG. 7 is a sectional view of a portion of the distal femur multiple resection guide of the present invention shown attached to a distal femur and showing a reciprocating saw being guided to make an anterior bevel cut.

FIG. 8 is a sectional view of a portion of the distal femur multiple resection guide of the present invention shown attached to a distal femur and showing a reciprocating saw being guided to make a posterior condyle cut.

FIG. 9 is a sectional view of a portion of the distal femur multiple resection guide of the present invention shown attached to a distal femur and showing a reciprocating saw being guided to make a patellar track groove cut.

FIG. 10 is a perspective view of the distal femur multiple resection guide of the present invention shown attached to a distal femur and showing an endmill being guided to make a posterior stabilized cut.

FIG. 11 is a perspective view of the distal femur multiple resection guide of the present invention shown attached to a distal femur and showing a housing punch being guided to finish a posterior stabilized cut.

DESCRIPTION OF THE PREFERRED EMBODIMENT

Figure 1:
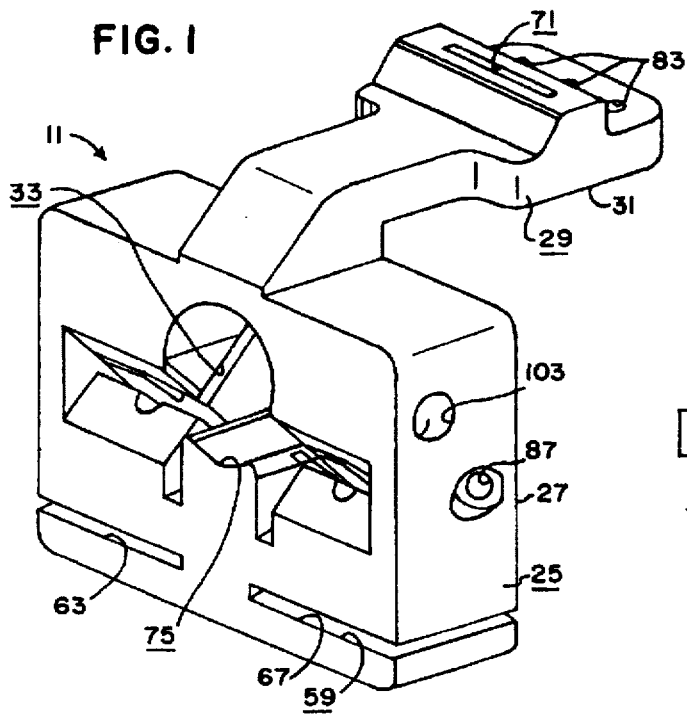
FIG. 1 is a perspective view of the distal femur multiple resection guide of the present invention.
Figure 2:
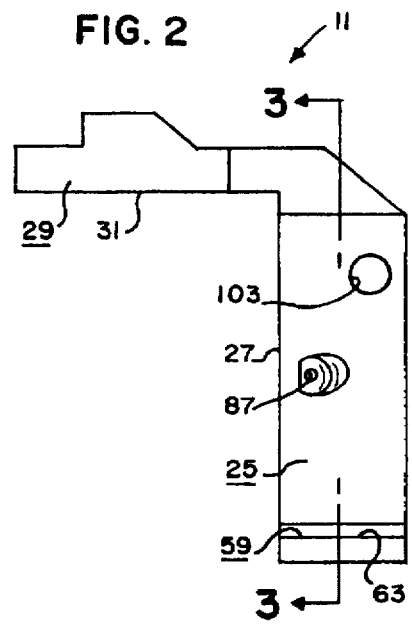
FIG. 2 is a side elevation view of the distal femur multiple resection guide of the present invention.
Figure 3:
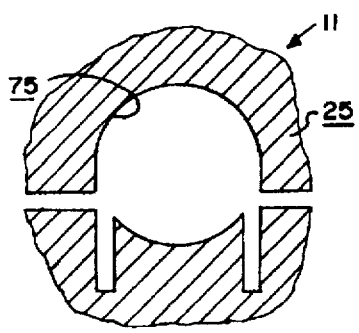
FIG. 3 is a sectional view of a portion of the distal femur multiple resection guide of the present invention substantially as taken on line 3—3 of FIG. 1.
Figure 4:
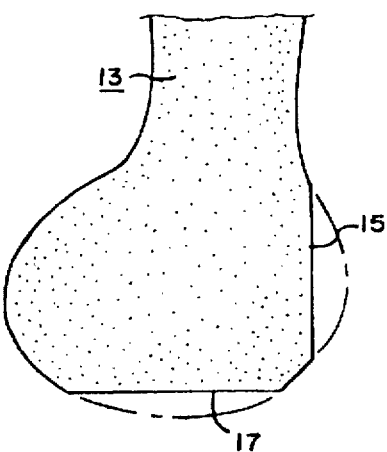
FIG. 4 is a side view of a distal femur having an anterior condyle resection and a distal femoral resection with the resected portions shown in broken lines for clarity.

A preferred embodiment of the distal femur multiple resection guide of the present invention is shown in FIGS. 1–11, and identified by the numeral 11. The distal femur multiple resection guide 11 is especially designed for attachment to a distal femur 13 having a resected anterior surface 15 and a resected distal surface 17, and for guiding one or more cutting tools such as an oscillating saw 19 (see FIGS. 6–9), endmill 21 (see FIG. 10), housing punch 23 (see FIG. 11), etc.

The multiple resection guide 11 includes a block member 25 having a distal femoral resection contact surface 27 for placement against the resected distal surface 17 of the distal femur 13. The contact surface 27 is preferably shaped to stably contact at least a substantial portion of the resected distal surface 17. As known to those skilled in the art, the resected distal surface 17 typically has a substantially planar face and the contact surface 27 preferably has a substantially planar face for placement against the substantially planar face of the resected distal surface 17 so that the block member 25 can be stably abutted against the distal femur 13 as will now be apparent to those skilled in the art.

The multiple resection guide 11 includes an arm member 29 having an anterior resection contact surface 31 for placement against the resected anterior surface 15 of the distal femur 13. The contact surface 31 is preferably shaped to stably contact at least a substantial portion of the resected anterior surface 15. As known to those skilled in the art, the resected anterior surface 15 typically has a substantially planar face and the contact surface 31 preferably has a substantially planar face for placement against the substantially planar face of the resected anterior surface 15 so that the arm member 29 can be stably abutted against the distal femur 13 as will now be apparent to those skilled in the art.

The block member 25 and arm member 29 may be constructed in various specific designs, in various sizes and out of various materials in various manners. Preferably, the block member 25 and arm member 29 are machined out of stainless steel or the like as a one-piece, integral unit in the design substantially shown in the drawings.

The multiple resection guide 11 includes anterior bevel cut guide means 33 on the block member 25 for guiding the cutting tool to make an anterior bevel cut 35 on the distal femur 13. The anterior bevel cut guide means 33 preferably includes a medial anterior bevel cut guide means 37 for guiding the cutting tool to make a medial anterior bevel cut 39 on the distal femur 13, and a lateral anterior bevel cut guide means 41 for guiding the cutting tool to make a lateral anterior bevel cut 43 on the distal femur 13. The anterior bevel cut guide means 33 preferably consist of one or more slots through the block member 25 in the appropriate location and at the appropriate angle to guide a cutting blade 45 of the oscillating saw 19 through the appropriate medial and lateral portions of the anterior surface of the distal femur 13 to correctly make the medial and lateral anterior bevel cuts 39, 43 as will now be apparent to those skilled in the art.

The multiple resection guide 11 includes posterior bevel cut guide means 47 on the block member 25 for guiding the cutting tool to make a posterior bevel cut 49 on the distal femur 13. The posterior bevel cut guide means 47 preferably includes a medial posterior bevel cut guide means 51 for guiding the cutting tool to make a medial posterior bevel cut 53 on the distal femur 13, and a lateral posterior bevel cut guide means 55 for guiding the cutting tool to make a lateral posterior bevel cut 57 on the distal femur 13. The posterior bevel cut guide means 47 preferably consist of one or more slots through the block member 25 in the appropriate location and at the appropriate angle to guide the cutting blade 45 of the oscillating saw 19 through the appropriate medial and lateral portions of the posterior surface of the distal femur 13 to correctly make the medial and lateral posterior bevel cuts 53, 57 as will now be apparent to those skilled in the art.

The multiple resection guide 11 includes posterior condyle cut guide means 59 on the block member 25 for guiding the cutting tool to make a posterior condyle cut 61 on the distal femur 13. The posterior condyle cut guide means 59 preferably includes a medial posterior condyle cut guide means 63 for guiding the cutting tool to make a medial posterior condyle cut 65 on the distal femur 13, and a lateral posterior condyle cut guide means 67 for guiding the cutting tool to make a lateral posterior condyle cut 69 on the distal femur 13. The posterior condyle cut guide means 59 preferably consist of one or more slots through the block member 25 in the appropriate location and at the appropriate angle to guide the cutting blade 45 of the oscillating saw 19 through the appropriate medial and lateral condyle portions of the posterior surface of the distal femur 13 to correctly make the medial and lateral posterior condyle cuts 65, 69 as will now be apparent to those skilled in the art.

The multiple resection guide 11 includes patellar track cut guide means 71 on the arm member 29 for guiding the cutting tool to make a patellar track cut 73 on the distal femur 13. The patellar track cut guide means 71 preferably consist of a slot through the arm member 29 in the appropriate location (e.g., an anterior slot) and at the appropriate angle to guide the cutting blade 45 of the oscillating saw 19 through the appropriate portions of the distal femur 13 to correctly make the patellar track cut 73 as will now be apparent to those skilled in the art.

The multiple resection guide 11 preferably includes posterior stabilized cut guide means 75 on the block member 25 for guiding the cutting tool to make a posterior stabilized cut 77 on the distal femur 13. The posterior stabilized cut guide means 75 preferably includes a bore through the block member 25 in the appropriate location and at the appropriate angle to guide a reamer 79 of the endmill 21 through the appropriate portions of the distal femur 13 to correctly make the posterior stabilized cut 77 as will now be apparent to those skilled in the art. In addition, the posterior stabilized cut guide means 75 preferably includes a pair of slots extending through the block member 25 on opposite sides of the bore in the appropriate location and at the appropriate angle to guide a cutting head 81 of the housing punch 23 through the appropriate portions of the distal femur 13 to correctly finish the posterior stabilized cut 77 as will now be apparent to those skilled in the art.

The multiple resection guide 11 preferably includes means for allowing the block member 25 and arm member 29 to be attached to the distal femur 13. More specifically, the multiple resection guide 11 preferably has one or more apertures 83 through the arm member 29 for allowing bone pins or screws 85 or the like to be used to securely attach the block member 25 and arm member 29 to the distal femur 13. In addition, the multiple resection guide 11 preferably has one or more apertures 87 through the block member 25 for allowing bone clamps 89, bone screws 85 (not shown), or the like to be used to securely attach the block member 25 and arm member 29 to the distal femur 13.

The multiple resection guide 11 preferably includes external alignment guide means 91 for verifying alignment of the block member 25 and arm member 29 relative to the longitudinal axis 93 of the distal femur 13. The external alignment guide means 91 preferably includes a base member 95 for attachment to the arm member 29 and preferably includes an elongated alignment pin member or means 97 having an longitudinal axis 99 for attachment to the base member 95 with the longitudinal axis 99 thereof substantially perpendicular to the distal femoral resection contact surface 27 of the block member 25 and for providing a visual guide that the block member 25 and arm member 29 are properly aligned relative to the longitudinal axis 93 of the distal femur 13.

The multiple resection guide 11 preferably includes one or more handle members or means 101 for enhancing control and placement of the multiple resection guide 11 relative to the distal femur 13. More specifically, the block member 25 may have one or more threaded apertures 103 therein and each handle member 101 may include a threaded end (not shown) for be selectively screwed into a threaded aperture 103 when desired.

The preferred method of making the desired resections on a distal femur 13 of the present invention is as follows: First, preoperative planning and exposure of the distal femur 13 is done in any normal manner such as, for example, as disclosed at pages 2 and 3 in the document, *Total Condylar & Posterior Stabilized Surgical Technique, ORTHOLOC® ADVANTIM™*, Wright Medical Technology, Inc. (1993). The distal femur 13 can then be cut to form the resected anterior surface 15 and resected distal surface 17 in any manner now apparent to those skilled in the art such as, for example, by using the surgical techniques and instrumentation disclosed in FIGS. 4–8 and described, in general, at columns 9–13 of Dunn, U.S. Pat. No. 4,759,350, issued Jul. 26, 1988, incorporated herein by reference. A multiple resection guide 11 corresponding to the selected implant size is then placed on the distal femur 13 with the distal femoral resection contact surface 27 of the block member 25 placed against the resected distal surface 17 of the distal femur 13 and with the anterior resection contact surface 31 of the arm member 29 placed against the resected anterior surface 15 of the distal femur 13. Component size selection can be intraoperatively confirmed by evaluating the anterior/posterior and medial/lateral coverage of various different sizes of multiple resection guides 11 as will now be apparent to those skilled in the art. In general, one to two millimeters of lateral posterior condyle should be visible under the posterior edge of the multiple resection guide 11 with approximately three to four millimeters of posterior condyle visible under the medial side of the multiple resection guide 11. If more that two millimeters of lateral posterior condyle is visible under the multiple resection guide 11, a larger implant size and a larger multiple resection guide 11 size should be considered. If no lateral posterior condyle is visible, a smaller implant size and a smaller multiple resection guide 11 size should be considered. The multiple resection guide 11 is then fixed to the anterior portion of the distal femur 13 using bone screws 85 or the like. Then, using additional bone screws 85 and/or bone clamps 89, etc., the multiple resection guide 11 is fixed to the distal portion of the distal femur 13 to ensure accurate resections, which are pertinent to the appropriate fit of the femoral implant, etc. Handle members 101 may be attached to the block member 25 and used for extra support, if necessary, to aid in proper positioning and attachment of the multiple resection guide 11 to the distal femur 13. If desired, before any cuts are made, the base member 95 of the external alignment guide means 91 can be attached to the arm member 29 and the elongated alignment pin means 97 used to verify alignment of the block member 25 and arm member 29 relative to the longitudinal axis 93 of the distal femur 13 as will now be apparent to those skilled in the art. Once the multiple resection guide 11 is securely affixed to the distal femur 13, the various bevel and posterior resections are made. The anterior bevel cuts 39, 43 are preferably made using a wide cutting blade 45 The posterior bevel cuts 51, 57 and posterior condyle cuts 65, 69 are preferably made using a narrow cutting blade 45 to minimize the chance of ligament damage. The cutting blade 45 can be passed over the cut surface several times to ensure that the cutting blade 45 has not been diverted by hard bone, etc. With the multiple resection guide 11 still in place, the trochlear groove is recessed by inserting a narrow cutting blade 45 through the patellar track cut guide means 71 of the multiple resection guide 11 to form the patellar track cut 73. The cutting blade 45 is passed across the resection several times to ensure a thorough resection. If a posterior stabilized prosthesis is to be implanted, the multiple resection guide is left in place and the reamer 79 of the endmill 21 is placed into the posterior stabilized cut guide means 75. The endmill 21 is brought to full speed before contacting bone. The reamer 79 is inserted until it is fully seated against the block member 25. Periodically, some bone may remain posterior to the endmill cut. The cutting head 81 of the housing punch 23 is used to remove such remaining bone. The cutting head 81 is inserted until a "maximum depth" line 105 on the side of the housing punch 23 is even with the surface of the outer surface of the block member 25. The multiple resection guide 11 is then removed from the distal femur 13 and a chisel, rongeur or saw blade may be used to remove any remaining ridges, etc., in the patellar track cut 73 and/or the posterior stabilized cut 77. The distal femur 13 is then ready to receive a prosthetic implant in any manner now apparent to those skilled in the art.

Although the present invention has been described and illustrated with respect to a preferred embodiment and a preferred use therefor, it is not to be so limited since modifications and changes can be made therein which are within the full intended scope of the invention.

We claim:

1. A distal femur multiple resection guide for attachment to a distal femur having a resected anterior surface and a resected distal surface, and for guiding a cutting tool; the multiple resection guide comprising:

(a) a block member having a distal femoral resection contact surface for placement against the resected distal surface of the distal femur;

(b) an arm member having opposite sides and having an anterior resection contact surface for placement against the resected anterior surface of the distal femur;

(c) anterior bevel cut guide means on the block member for guiding the cutting tool to make an anterior bevel cut on the distal femur;

(d) posterior bevel cut guide means on the block member for guiding the cutting tool to make a posterior bevel cut on the distal femur;

(d) posterior condyle cut guide means on the block member for guiding the cutting tool to make a posterior condyle cut on the distal femur; and (e) patellar track cut guide means on the arm member for guiding the cutting tool to make a patellar track cut on the distal femur; the patellar track cut guide means including a slot through the arm member substantially midway between the opposite sides of the arm member; the slot through the arm member having a guide surface for guiding the cutting tool; the plane of the guide surface of the slot through the arm member forming an oblique angle to the plane of the anterior resection contact surface of the arm member.

2. The multiple resection guide of claim 1 in which is included posterior stabilized cut guide means on the block member for guiding the cutting tool to make a posterior stabilized cut on the distal femur; the posterior stabilized cut guide means including a bore through the block member, the bore through the block member including an anterior guide surface, a posterior guide surface, a first side guide surface, and a second side guide surface said first and second side guide surfaces each having a portion tangent to the anterior guide surface.

3. The multiple resection guide of claim 1 in which is included means for allowing the block member and arm member to be attached to the distal femur.

4. The multiple resection guide of claim 1 in which the anterior bevel cut guide means includes a medial anterior bevel cut guide means for guiding the cutting tool to make a medial anterior bevel cut on the distal femur; and in which the anterior bevel cut guide means includes a lateral anterior bevel cut guide means for guiding the cutting tool to make a lateral anterior bevel cut on the distal femur.

5. The multiple resection guide of claim 1 in which the posterior bevel cut guide means includes a media/posterior bevel cut guide means for guiding the cutting tool to make a medial posterior bevel cut on the distal femur; and in which the posterior bevel cut guide means includes a lateral anterior bevel cut guide means for guiding the cutting tool to make a lateral posterior bevel cut on the distal femur.

6. The multiple resection guide of claim 1 including external alignment guide means for verifying alignment of the block member and arm member relative to the longitudinal axis of the distal femur.

7. The multiple resection guide of claim 6 in which the external alignment guide means includes a base member for attachment to the arm member and includes an elongated alignment pin means having a longitudinal axis for attachment to the base member with the longitudinal axis thereof substantially perpendicular to the distal femoral resection contact surface of the block member and for providing a visual guide that the block member and arm member are properly aligned relative to the longitudinal axis of the distal femur.

8. The multiple resection guide of claim 1 including handle means for attachment to the block member.

9. A distal femur multiple resection guide for attachment to a distal femur having a resected anterior surface and a resected distal surface, and for guiding an oscillating saw and a reamer; the multiple resection guide comprising:

(a) a block member having a distal femoral resection contact surface for placement against the resected distal surface of the distal femur;

the block having a medial anterior bevel cut slot for guiding the oscillating saw to make a medial anterior bevel cut on the distal femur;

the block having a lateral anterior bevel cut slot for guiding the oscillating saw to make a lateral anterior bevel cut on the distal femur;

the block having a medial posterior bevel cut slot for guiding the oscillating saw to make a medial posterior bevel cut on the distal femur;

the block having a lateral posterior bevel cut slot for guiding the oscillating saw to make a lateral posterior bevel cut on the distal femur;

the block having a medial posterior condyle cut slot for guiding the oscillating saw to make a medial posterior condyle cut on the distal femur;

the block having a lateral posterior condyle cut slot for guiding the oscillating saw to make a lateral posterior condyle cut on the distal femur;

the block having a posterior stabilized cut aperture for guiding the reamer to make a posterior stabilized cut on the distal femur; said posterior stabilized cut aperture having an anterior guide surface, a posterior guide surface, a first side guide surface, and a second side guide surface; and said first and second side guide surfaces each having a portion orthogonal to the media and lateral posterior condyle cut slots, (b) an arm member having an anterior resection contact surface for placement against the resected anterior surface of the distal femur;

the arm member having a patellar track cut slot for guiding the oscillating saw to make a patellar track cut on the distal femur.

10. The distal femur multiple resection guide of claim 9 including external alignment guide means for verifying alignment of the block member and arm member relative to the longitudinal axis of the distal femur.

11. The multiple resection guide of claim 10 in which the external alignment guide means includes a base member for attachment to the arm member and includes an elongated alignment pin means having a longitudinal axis for attachment to the base member with the longitudinal axis thereof substantially perpendicular to the distal femoral resection contact surface of the block member and for providing a visual guide that the block member and arm member are properly aligned relative to the longitudinal axis of the distal femur.

12. The multiple resection guide of claim 2 in which the posterior stabilized cut guide means includes a first slot extending from the first side guide surface of the bore through the block member to a point below the posterior guide surface of the bore through the block member, and includes a second slot extending from the second side guide surface of the bore through the block member to a point below the posterior guide surface of the bore through the block member.

13. The multiple resection guide of claim 9 in which the posterior stabilized cut guide means includes a first slot extending from the first side guide surface of the bore through the block member to a point below the posterior guide surface of the bore through the block member, and includes a second slot extending from the second side guide surface of the bore through the block member to a point below the posterior guide surface of the bore through the block member.

* * * * *